United States Patent
Beulay et al.

(10) Patent No.: US 8,557,113 B2
(45) Date of Patent: *Oct. 15, 2013

(54) CART AND INSTALLATION FOR TREATING BIOLOGICAL LIQUID

(75) Inventors: Jean Luc Beulay, Krautergersheim (FR); Virginie Buisson, Wolfisheim (FR); Sebastien Cirou, Schiltigheim (FR); Cecile Delbos, Eschau (FR); Marc Hlavacek, Phalsbourg (FR); Frans Mels, Altenmarkt (FR); Rene Reinbigler, Kirchheim (FR); Jean Louis Weissenbach, Barr (FR)

(73) Assignee: EMD Millipore Corporation, Billerica, MA (US)

( * ) Notice: Subject to any disclaimer, the term of this patent is extended or adjusted under 35 U.S.C. 154(b) by 598 days.

This patent is subject to a terminal disclaimer.

(21) Appl. No.: 12/592,901

(22) Filed: Dec. 4, 2009

(65) Prior Publication Data

US 2010/0206785 A1    Aug. 19, 2010

(51) Int. Cl.
*B01D 17/12* (2006.01)
*B01D 35/02* (2006.01)
*B01D 36/04* (2006.01)

(52) U.S. Cl.
USPC ............ 210/257.1; 137/255; 137/565.29; 137/571; 210/416.1; 210/258; 210/262; 435/297.1; 435/307.1

(58) Field of Classification Search
USPC ............ 137/255, 565.29, 565.3, 571, 576; 210/85, 86, 143, 17, 205, 206, 241, 210/257.1, 258, 261, 262, 348, 416.13, 210/416.3; 422/501, 527, 534, 535; 435/289.1, 297.1, 307.1, 308.1; 366/278

See application file for complete search history.

(56) References Cited

U.S. PATENT DOCUMENTS

| 2,413,853 | A | * | 1/1947 | Clarke et al. ............ 134/115 R |
| 3,022,229 | A |   | 2/1962 | Heden |
| 3,179,117 | A | * | 4/1965 | Gibson et al. ............ 134/107 |
| 3,667,487 | A | * | 6/1972 | Schoenbeck et al. ...... 134/108 |
| 4,113,623 | A |   | 9/1978 | Koether et al. |

(Continued)

FOREIGN PATENT DOCUMENTS

DE    102006059459 A1    7/2008
DE    102008003823 A1    7/2008

(Continued)

OTHER PUBLICATIONS

Extended European Search Report received for EP Patent Application No. 09290938.1, mailed on Apr. 6, 2010, 5 pages.

(Continued)

*Primary Examiner* — Joseph Drodge
(74) *Attorney, Agent, or Firm* — EMD Millipore Corporation

(57) ABSTRACT

The cart comprises a lateral face by which it is adapted to be juxtaposed against another cart. It further comprises a first pump, a second pump disposed below said first pump and laterally offset relative thereto, and a tank adapted to receive a feed container provided to contain said biological liquid, said tank being disposed above said first pump and offset laterally relative thereto. The installation comprises one said cart, a filter and a second cart, juxtaposed against said first cart and of which the upper face supports said filter such that an outlet point of said first pump is situated substantially facing an inlet/outlet aperture of said filter.

16 Claims, 7 Drawing Sheets

(56) References Cited

U.S. PATENT DOCUMENTS

| | | | |
|---|---|---|---|
| 4,332,750 A | | 6/1982 | Roggenburg, Jr. et al. |
| 4,784,751 A | * | 11/1988 | McGehee .................... 208/181 |
| 4,852,851 A | | 8/1989 | Webster |
| 4,855,236 A | * | 8/1989 | Levin .......................... 435/430 |
| 4,915,119 A | * | 4/1990 | Franklin ..................... 134/57 R |
| 5,141,866 A | * | 8/1992 | Levin .......................... 435/430 |
| 5,265,912 A | * | 11/1993 | Natividad ..................... 280/828 |
| 5,290,518 A | | 3/1994 | Johnson |
| 5,342,463 A | | 8/1994 | Addeo et al. |
| 5,520,885 A | | 5/1996 | Coelho et al. |
| 5,985,653 A | * | 11/1999 | Armstrong et al. ........ 435/303.1 |
| 6,129,099 A | * | 10/2000 | Foster et al. ................ 134/57 R |
| 6,146,124 A | | 11/2000 | Coelho et al. |
| 6,213,334 B1 | | 4/2001 | Coelho et al. |
| 6,228,255 B1 | * | 5/2001 | Peterson et al. .................. 210/90 |
| 6,232,115 B1 | | 5/2001 | Coelho et al. |
| 6,303,025 B1 | * | 10/2001 | Houchens ..................... 210/104 |
| 6,361,642 B1 | | 3/2002 | Bellamy et al. |
| 6,808,675 B1 | | 10/2004 | Coelho et al. |
| 6,902,706 B1 | | 6/2005 | Colin et al. |
| 7,485,224 B2 | * | 2/2009 | Jones et al. ................... 210/241 |
| 7,935,253 B2 | * | 5/2011 | Beulay et al. ................. 210/241 |
| 8,163,172 B2 | * | 4/2012 | Beulay et al. ................... 210/90 |
| 8,343,356 B2 | | 1/2013 | Beulay et al. |
| 2004/0031507 A1 | * | 2/2004 | Ross et al. .................... 134/123 |
| 2004/0104153 A1 | | 6/2004 | Yang |
| 2004/0259240 A1 | * | 12/2004 | Fadden ....................... 435/297.3 |
| 2005/0254879 A1 | | 11/2005 | Gundersen et al. |
| 2006/0024212 A1 | | 2/2006 | Hwang |
| 2006/0057030 A1 | | 3/2006 | Lee et al. |
| 2006/0118472 A1 | | 6/2006 | Schick et al. |
| 2007/0095364 A1 | * | 5/2007 | Watt ................................ 134/10 |
| 2007/0112297 A1 | | 5/2007 | Plahey et al. |
| 2007/0128087 A1 | * | 6/2007 | Cannizzaro et al. .......... 422/119 |
| 2007/0199875 A1 | | 8/2007 | Moorey et al. |
| 2008/0057274 A1 | | 3/2008 | Hagiwara et al. |
| 2008/0213143 A1 | | 9/2008 | Gyonouchi et al. |
| 2008/0254962 A1 | | 10/2008 | Mizuo et al. |
| 2009/0101552 A1 | | 4/2009 | Fulkerson et al. |
| 2009/0294349 A1 | | 12/2009 | Beulay et al. |
| 2009/0314970 A1 | | 12/2009 | Mcavoy et al. |
| 2010/0126927 A1 | | 5/2010 | Blankenstein et al. |
| 2011/0297866 A1 | | 12/2011 | Weber |
| 2011/0303306 A1 | | 12/2011 | Weber |
| 2012/0006736 A1 | | 1/2012 | Cirou et al. |
| 2012/0018018 A1 | | 1/2012 | Cirou et al. |
| 2012/0031510 A1 | | 2/2012 | Weissenbach et al. |
| 2012/0138173 A1 | | 6/2012 | Cirou et al. |
| 2012/0138522 A1 | | 6/2012 | Cirou et al. |
| 2012/0145616 A1 | | 6/2012 | Weissenbach et al. |
| 2012/0160342 A1 | | 6/2012 | Weissenbach et al. |
| 2012/0160356 A1 | | 6/2012 | Reinbigler et al. |
| 2012/0248025 A1 | | 10/2012 | Reinbigler et al. |

FOREIGN PATENT DOCUMENTS

| | | | |
|---|---|---|---|
| EP | 0479047 | A2 | 4/1992 |
| EP | 0803723 | A1 | 10/1997 |
| EP | 1195171 | A2 | 4/2002 |
| EP | 1239277 | A1 | 9/2002 |
| EP | 2044964 | A2 | 4/2009 |
| EP | 2130903 | A1 | 12/2009 |
| EP | 2208534 | A1 | 7/2010 |
| EP | 2228635 | A1 | 9/2010 |
| FR | 2241615 | A1 | 3/1975 |
| FR | 2673853 | A1 | 9/1992 |
| FR | 2931838 | A1 | 12/2009 |
| FR | 2940145 | A1 | 6/2010 |
| GB | 1434786 | A | 5/1976 |
| GB | 2448858 | A | 11/2008 |
| JP | 62-81543 | A | 4/1987 |
| WO | 00/48703 | A1 | 8/2000 |
| WO | 2005/090403 | A2 | 9/2005 |
| WO | 2006/043895 | A1 | 4/2006 |
| WO | 2008/064242 | A2 | 5/2008 |
| WO | 2008/071351 | A1 | 6/2008 |
| WO | 2009/017614 | A1 | 2/2009 |
| WO | 2009073567 | A1 | 6/2009 |
| WO | 2009/157852 | A1 | 12/2009 |
| WO | 2010/084432 | A1 | 7/2010 |
| WO | 2010/094249 | A1 | 8/2010 |

OTHER PUBLICATIONS

Search Report received for French Patent Application No. 0853629, mailed on Feb. 9, 2009, 2 pages.

Search Report and Written Opinion received for French Patent Application No. 1056421, mailed on May 24, 2011, 2 pages.

Search Report received for French Patent Application No. 1054516, mailed on Nov. 22, 2010, 6 pages.

Search Report received for French Patent Application No. 1054517, mailed on Nov. 22, 2010, 6 pages.

Search Report received for French Patent Application No. 1050209, mailed on Sep. 24, 2010, 6 pages.

Search Report received for French Patent Application No. 1055025, mailed on Nov. 12, 2010, 5 pages.

Search Report received for French Patent Application No. 1055026, mailed on Feb. 3, 2011, 6 pages.

Search Report received for French Patent Application No. 1054514, mailed on Nov. 25, 2010, 6 pages.

Search Report received for French Patent Application No. 1152556, mailed on Nov. 17, 2011.

International Search report and Written Opinion received for PCT Application No. PCT/IB2011/052447, mailed on Sep. 30, 2011, 9 pages.

International Search Report and Written Opinion received for PCT patent Application No. PCT/IB2011/052450, mailed on Sep. 28, 2011, 11 pages.

International Search Report received for PCT Patent Application No. PCT/IB2011/050089, mailed on Jun. 8, 2011, 4 pages.

International Search Report received for PCT Patent Application No. PCT/IB2011/052676, mailed on Sep. 29, 2011, 3 pages.

International Search Report received for PCT Patent Application No. PCT/IB2011/052679, mailed on Aug. 29, 2011, 3 pages.

International Search Report received for PCT Patent Application No. PCT/IB2011/052448, mailed on Aug. 2, 2011, 4 pages.

Beulay et al., "Installation for Treating a Biological Liquid", unpublished U.S. Appl. No. 13/420,906, filed Mar. 15, 2012, 24 pages.

French Search Report received for French Patent Application No. 0950435, mailed on Oct. 16, 2009, 2 pages.

Extended European Search Report and Search Opinion received for EP Patent Application No. 10290005.7, mailed on May 17, 2010, 5 pages.

International Preliminary Report on Patentability received for PCT Patent Application No. PCT/IB2010/050102, mailed on Aug. 4, 2011, 8 pages.

International Search Report and Written Opinion received for PCT Patent Application No. PCT/IB2010/050102, mailed on May 7, 2010, 10 pages.

International Preliminary Report on Patentability received for PCT Patent Application No. PCT/IB2011/050089, mailed on Jul. 26, 2012, 7 pages.

International Written Opinion received for PCT Patent Application No. PCT/IB2011/050089, mailed on Jun. 8, 2011, 5 pages.

International Preliminary Report on Patentability received for PCT Patent Application No. PCT/IB2011/052447, mailed on Dec. 20, 2012, 6 pages.

International Preliminary Report on Patentability received for PCT Patent Application No. PCT/IB2011/052448, mailed on Dec. 20, 2012, 6 pages.

International Written Opinion received for PCT Patent Application No. PCT/IB2011/052448, mailed on Aug. 2, 2011, 4 pages.

International Preliminary Report on Patentability received for PCT Patent Application No. PCT/IB2011/052450, mailed on Dec. 20, 2012, 8 pages.

(56) References Cited

OTHER PUBLICATIONS

International Preliminary Report on Patentability received for PCT Patent Application No. PCT/IB2011/052676, mailed on Jan. 10, 2013, 7 pages.
International Written Opinion received for PCT Patent Application No. PCT/IB2011/052676, mailed on Sep. 29, 2011, 5 pages.
International Preliminary Report on Patentability received for PCT Patent Application No. PCT/IB2011/052679, mailed on Jan. 10, 2013, 8 pages.
International Written Opinion received for PCT Patent Application No. PCT/IB2011/052679, mailed on Aug. 29, 2011, 6 pages.
International Search Report received for PCT Patent Application No. PCT/IB2012/051424, mailed on Sep. 4, 2012, 3 pages.

* cited by examiner

CART AND INSTALLATION FOR TREATING BIOLOGICAL LIQUID

CROSS-REFERENCED TO RELATED APPLICATIONS

This application claims the benefit of French Patent Application No.: 0859079, filed on Dec. 24, 2008 the entire contents of which are incorporated by reference herein.

DESCRIPTION OF THE INVENTION

Field of the Invention

The invention relates to installations for treating a biological liquid, in particular, but not exclusively, for purifying a biopharmaceutical liquid in order to obtain products such as monoclonal antibodies, vaccines or recombinant proteins.

It is known that biopharmaceutical liquids are in general obtained by culture in a bioreactor and that they must then be purified to achieve the required characteristics of purity, concentration, absence of viruses, etc.

The purification is carried out by a succession of treatments such as clarification, to eliminate the residues from the bioreactor culture, and viral filtration sometimes followed by diafiltration and concentration by tangential flow filtration (TFF). Other operations exist concerning purification, such as chromatography and sterile filtration (to remove bacteria).

The purification treatments are essentially carried out by filtering operations in a circuit leading to a container for collecting the treated liquid.

A number of types of container containing liquids can be connected to the inlet of the circuit, such as the source container that contains the product to be treated, but also containers containing a cleaning liquid such as sodium hydroxide (NaOH), a rinsing liquid such as pure water or a buffer liquid such as a saline solution. In addition to the container for collecting the treated liquid, various other containers for collecting cleaning, rinsing or buffer liquid, or for collecting residues, can be connected to the outlet of the circuit.

In a production context the liquid treatments can be carried out sequentially, the collecting container for the first treatment potentially becoming the source container for the next treatment, and so on until the last treatment is carried out.

These treatments are conventionally carried out in dedicated circuits, with stainless steel pipes and other components such as tanks and filter housings, which necessitate operations before and after the actual treatment, which are relatively onerous, in particular operations of cleaning after use.

The invention aims to provide an installation for treating a biological liquid that is particularly simple, convenient and effective.

It provides, according to a first aspect, a cart for a biological liquid treatment installation characterized in that it comprises a first lateral face, a second lateral face by which it is adapted to be juxtaposed against another cart and a front face which meets the two said lateral faces;

said cart further comprising:
a first pump;
a second pump disposed below said first pump and laterally offset relative thereto towards said first lateral face; and
a tank disposed above said first pump and offset laterally relative thereto towards said first lateral face, said tank being adapted to receive a feed container provided to contain said biological liquid.

The feed container is provided to be linked by flexible disposable pipes to said pumps and to other elements of said installation, at least one of said other elements (e.g. a filter) being provided to be disposed on said other cart.

The installation which the cart according to the invention enables to be obtained is provided to comprise disposable elements, for the most part flexible ("Flexware™ products"), among which are the feed container for liquid to treat, a collecting container for treated liquid, sections of circuit including the disposable pipes as well as a filter or filter elements; and permanent or reusable elements ("hardware"), arranged in part on the cart according to the invention.

The assembly of such an installation is made simply by equipping the hardware, including the cart according to the invention, with the disposable elements, which comprise the components adapted to cooperate with the pumps (e.g. certain disposable pipes if the pumps are of the peristaltic type) and the feed container adapted to be received in the tank.

The arrangement of these permanent elements on the cart is also predetermined to be particularly convenient and efficient. The second pump and the tank are thus each offset relative to the reference element constituted by the first pump.

The position of that first pump is dictated by that of the main elements of the installation (such as the filter or filters) with which it cooperates and which are disposed on the other cart (or on any other support such as a table able to be juxtaposed against the cart according to the invention).

This arrangement ensures, firstly, fast mounting (and disassembly) of the installation by facilitating the connections and by limiting pipe crossings.

It also enables significant reduction in the length of the disposable pipes linking the pumps and the feed container to mount in the tank as well as the length of certain disposable pipes linking the pumps and the feed container to the other elements of the installation.

In particular, the relative positioning between the tank and the first pump is provided in order for the flexible disposable pipe linking that pump to the feed container to be as short as possible while respecting a minimum radius of curvature in order to avoid any risk of pinching.

The reduction in the length of the disposable pipes enables the volume of biological liquid present in the pipes to be reduced. This makes it possible for example to achieve a smaller final volume in the case in which a treatment is carried out in which flow occurs in a loop to which belong the feed container and a filter from which the filtrate is evacuated, since at the end of treatment the feed container is empty or nearly so and the liquid is essentially present in the pipes. This reduction in the final volume enables a higher level of concentration to be attained.

Lastly, the disposition of these re-usable elements on several superposed levels enables optimization of the floor space ("footprint") required for the installation.

This possibility given by the cart according to the invention of optimizing the footprint is particularly advantageous when, as is generally the case in operations for treatment of biopharmaceutical liquids, the installation is placed in an area of controlled atmosphere where space is limited and very costly.

According to features preferred for reasons of simplicity and convenience of implementation:
said second pump is offset depthwise relative to said first pump towards said front face;
said tank is movably mounted between an upright service position for the operations of treating said biological liquid, and a lying-down installation position for the mounting or withdrawal of said feed container;
said tank is adapted to pivot about an axis perpendicular to said front face of said cart;

said cart comprises means for locking said tank in either of the positions of service and installation;

said locking means comprise at least one pin;

said tank is mounted on a U-shaped bracket of which the ends are fixed to a balance frame adapted to cooperate with load cells to determine the mass of said tank;

said pumps are peristaltic pumps;

said cart comprises an electromagnetic drive to raise and turn a stir bar contained in said feed container;

said cart comprises a temperature probe for measuring, through said feed container, the temperature change of said biological liquid during said treatment; and/or said cart includes a control panel to control said pumps.

According to a second aspect, the invention is also directed to providing an installation for treating a biological liquid, comprising a cart as set forth above, designated first cart, a filter and a second cart, juxtaposed against said first cart, and of which the upper face supports said filter such that an outlet point of said first pump is situated substantially facing an inlet/outlet aperture of said filter.

The fact that an outlet point of the first pump is situated substantially facing the aperture of the filter enables optimization of the length of the disposable pipe linking that outlet point to that aperture.

Moreover, the support for that filter by the second cart makes it possible to facilitate the mounting of the installation according to the invention.

To be precise, it suffices for the operator to bring the two carts together in order for the main components of the installation (pumps, tank and filter) to be optimally positioned relative to each other. All that remains to do is to connect those components by installing the disposable elements, and the mounting of the installation is finished.

Lastly, just as preparation of the installation is facilitated by the arrangement of its main components in the two carts, the operations to be carried out on the installation, after the treatment operation that it has made possible to carry out, are particularly simple to implement because it is essentially a matter of scrapping the disposable elements with which the carts are equipped, the removal operations being just as simple to carry out as the mounting operations.

According to features that are preferred as being favorable to the simplicity and convenience of use of the installation of the invention:

said filter is a tangential filter;

said installation comprises a container for collecting said filtered biological liquid, said collecting container being disposed in a housing of said second cart;

said housing is formed by the interior of a drawer;

the facade of said drawer comprises a cut-out through which a flexible disposable pipe passes;

said installation comprises:

a source container for said biological liquid;

a feed container disposed in said tank of said cart;

a container for collecting said filtered biological liquid;

a transfer section for connecting said source container to a first aperture of a branching connector, comprising a member adapted to cooperate with said second pump of said cart to make said biological liquid flow;

a filling section linking a second aperture of said branching connector to an inlet/outlet aperture of said feed container;

a filtration section comprising said filter and connecting a third aperture of said branching connector to a first aperture of a second branching connector;

a feed section linking a second aperture of said second branching connector to an inlet/outlet aperture of said feed container, and comprising a member adapted to cooperate with said first pump of said cart to make said biological liquid flow; and a section for collecting said filtered liquid to link a third aperture of said second branching connector to said collecting container;

each of said transfer, filling, filtration, feed and collecting sections comprising at least one disposable pipe;

said installation comprises at least one section for conveying the filtrate that serves to link an outlet point of said filter to a waste container, comprising at least one disposable pipe; and/or said installation comprises two said conveying sections extending from a respective said outlet point of said filter and joining together via a branching connector so as to form a single section.

DESCRIPTION OF THE EMBODIMENTS

The disclosure of the invention will now be continued with the detailed description of an embodiment, given below by way of illustrative but non-limiting example, with reference to the accompanying drawings, in which.

Figure 1:
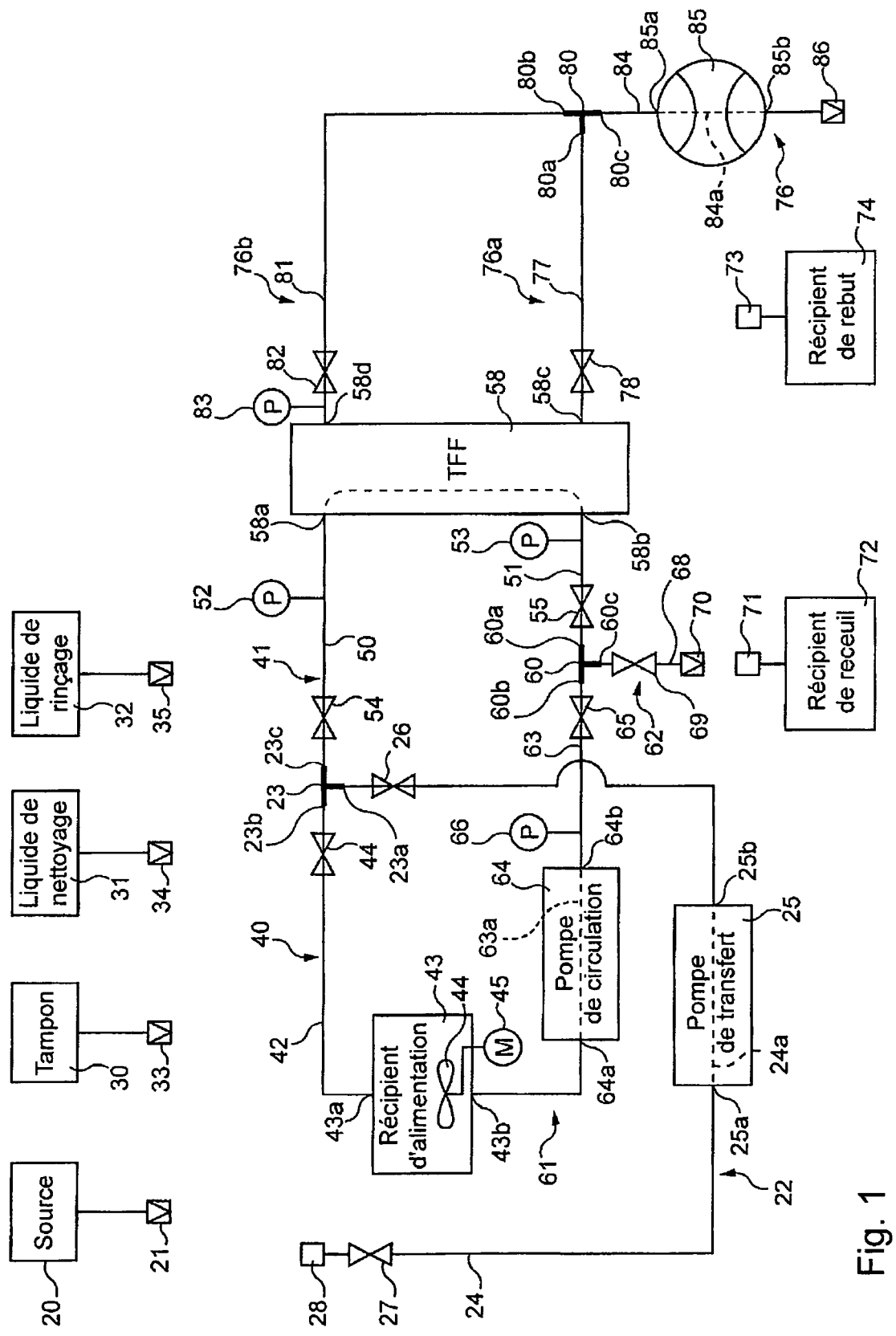
FIG. 1 is a diagrammatic view of a circuit of an installation for treatment by tangential filtration.

First of all, a description will be given with the aid of FIG. 1 of a circuit for treating a biological liquid by tangential filtration, produced using disposable elements installed on the two carts referred to above (the more detailed description of the installation will be given later).

The liquid to be treated is initially in a source bag 20, filled with liquid from the culture bioreactor or from the previous treatment. This source bag 20 is connectable via a male coupling connector 21 to a transfer section 22 which extends from a female coupling connector 28 to the first aperture 23a of a T-shaped branching connector 23.

This transfer section 22 comprises a disposable flexible pipe 24, a transfer pump 25 to make the liquid flow (here a peristaltic pump operating in the same way in both flow directions) and two isolation valves 26 and 27.

The term "pipe" must be understood in the present document as being a portion of tubing connecting two elements of the circuit, it being possible for this portion equally well to comprise a unique tube or on the contrary several tubes, possibly having different diameters, connected in series by a simple connector (not playing any other role here) or sophisticated connector (for example a disposable connector for a pressure sensor (or for a sensor of another physico-chemical value) or a disposable pump head).

Pipe 24 has a portion 24a passing right through pump 25 (from a first inlet/outlet point 25a to a second inlet/outlet point 25b) such that it may be compressed by said pump.

Valve 26 is implanted on pipe 24 near the branching connector 23 in order to allow or prevent the flow of liquid in the pipe 24.

Valve 27 is implanted on the pipe 24 close to the female coupling connector 28.

The operator has the possibility of connecting other bags 30, 31 and 32 to the transfer section 22, via male coupling connectors 33, 34 and 35 which may connect to the female coupling connector 28.

These bags 30, 31 and 32 respectively contain a buffer liquid (saline solution), a cleaning liquid (sodium hydroxide) and a rinsing liquid (water) to manage the state of cleanliness of the circuit or to push the treated liquid towards the elements which perform the treatment or towards the collecting container.

A filling section 40 and a filtration section 41 respectively extend from a second aperture 23b and from a third aperture 23c of the branching connector 23.

The filling section 40 which joins to an inlet/outlet aperture 43a of a flexible and disposable feed container 43, comprises a flexible and disposable pipe 42 and a valve 44 implanted on the pipe 42 close to the branching connector 23 (also disposable).

An agitator 44 actuated by an electromagnetic drive 45, is disposed in the container 43 in order to make the liquid contained therein homogenous.

The filtration section 41 which joins to a first aperture 60a of a T-shaped branching connector 60, comprises two disposable flexible pipes 50, 51, two connectors 52, 53 for pressure sensors, two isolation valves 54, 55 and the tangential filter 58.

Pipe 50 links the third aperture 23c of branching connector 23 to a first inlet/outlet aperture 58a of the filter 58. Connector 52 is inserted in series in pipe 50.

Pipe 51 links a second inlet/outlet aperture 58b of the filter 58 to the first aperture 60a of branching connector 60. Pressure sensor connector 53 is inserted in series in pipe 51.

The measurement made by the pressure sensor mounted on connector 53, in conjunction with the measurement made by the pressure sensor mounted on connector 52, enables the operational state of the tangential filter 58 to be known.

Valve 54 is implanted on pipe 50 close to branching connector 23, whereas valve 55 is implanted on pipe 51 close to branching connector 60.

A feed section 61 and a collecting section 62 respectively extend from a second aperture 60b and from a third aperture 60c of the branching connector 60.

The feed section 61 joins to an outlet aperture 43b of the feed container 43. It comprises a flexible and disposable pipe 63, a flow pump 64 to make the liquid flow (here, a peristaltic pump operating in the same way in both flow directions), a valve 65 implanted on pipe 63 close to branching connector 60, and a pressure sensor connector 66 inserted in series in pipe 63.

Pipe 63 has a portion 63a passing right through pump 64 (from an inlet point 64a to an outlet point 64b) such that it may be compressed by said pump.

The collecting section 62 joins to a male coupling connector 70. It solely comprises a flexible disposable pipe 68 and an isolation valve 69 implanted on pipe 68 close to branching connector 60.

Depending on the operations carried out, the male coupling connector 70 may be connected either to the female coupling connector 73 of a waste container 74, or to the female coupling connector 71 of a collecting connector.

The circuit for treatment by tangential filtration also comprises two sections 76a, 76b for conveying the filtrate which extend respectively from outlet points 58c and 58d of filter 58 and merge to form a single section 76 joining to a male coupling connector 86 which can be connected to the female coupling connector 73 of waste container 74.

Section 76a communicates with a first aperture 80a of a T-shaped branching connector 80. It comprises a flexible disposable pipe 77 and an isolation valve 78 implanted on pipe 77 close to filter 58.

Section 76b communicates with a second aperture 80b of the branching connector 80. It comprises a flexible disposable pipe 81, an isolating valve 82 implanted on pipe 81 close to filter 58, and a pressure sensor connector 83 inserted in series in pipe 81.

The measurement made by the pressure sensor mounted on connector 83, in conjunction with the measurements made by the pressure sensors mounted on the connectors 52 and 53, makes it possible to precisely verify the operational state of the tangential filter 58. Section 76 which extends from a third aperture 80c of the branching connector 80, comprises a flexible disposable pipe 84 and a flowmeter 85.

Pipe 84 has a portion 84a passing right through the flowmeter 85 (from an inlet point 85a to an outlet point 85b) such that the volume and the flow rate of the filtrate retrieved at the outlet of the filter 58 can be determined.

The operation of this circuit will now be described.

After the operations of cleaning and rinsing explained below, the treatment by tangential filtration can commence. Valves 54, 65 and 69 are closed in order to prevent any flow of liquid in the filtration section 41 and collecting section 62, the other valves being open.

The source bag 20 is linked to section 22 by the connection of a male coupling connector 21 to the female coupling connector 28.

The liquid to treat is next sucked from the source bag 20 by the transfer pump 25 and is conveyed to the feed container 43 via the transfer section 22 and filling section 40.

After the complete transfer of the liquid to treat into the circuit, the bag 30 containing the buffer liquid is connected via coupling connector 33 to coupling connector 28. This buffer liquid is then introduced into transfer section 22 thanks to transfer pump 25 in order to push the liquid to treat towards section 40 such that the totality of that liquid can be filtered and retrieved. Transfer section 22 is then isolated from the filling section 40 and filtration section 41 by closing valve 26.

Once the transfer has been carried out, valves 54 and 65 are opened, the liquid to treat is made to flow by the actuation of flow pump 64, in the sub-circuit formed by the feed section 61, filtration section 41 and filling section 40. After the passage of the liquid into the tangential filter 58, the retentate comes back to the feed container 43 whereas the filtrate is evacuated via sections 76a, 76b and 76 to be collected in the waste container 74.

The operation of making the liquid to treat flow into filter 58 is continued until the liquid attains the desired concentration.

The collection of the filtered liquid is then carried out in two successive sub-steps.

The first sub-step consists of retrieving the filtered liquid contained in the filtration section 41 and in the filter 58.

For this, valve 44 is closed whereas valve 26 is opened so as to place the transfer 22 and filtration 41 sections in communication, and to isolate them from the filling section 40.

In parallel, valve 65 is closed whereas valve 69 is opened so as to place the filtration 41 and collecting 62 sections in communication, and to isolate them from the feed section 61.

The male coupling connector 70 is connected to the female coupling connector 71 of the collecting container 72.

Buffer liquid is next conveyed in section 22 by virtue of transfer pump 25 in order to transfer the filtered liquid contained in the filtration section 41 and the filter 58, via the collecting section 62, to the collecting container 72.

The second sub-step consists of retrieving the filtered liquid contained in the filling 40 and feed 61 sections, and in the feed container 43.

For this, valve 54 is closed whereas valve 44 is opened so as to place the transfer 22 and filling 40 sections in communication, and to isolate them from the filtration section 41.

In parallel, valve 55 is closed whereas valve 65 is opened so as to place the feed 61 and collecting 62 sections in communication, and to isolate them from the filtration section 41.

Buffer liquid is then conveyed into section 22 by virtue of the transfer pump 25 in order to transfer the filtered liquid contained in the filling section 40 into the feed container 43.

The flow pump 64 next enables that liquid to be brought from container 43 to collecting container 72, via the feed 61 and collecting 62 sections.

A description will now be given of the cleaning and rinsing operations carried out prior to the treatment by tangential filtration to avoid any contamination of the biological liquid to treat.

In order to make the cleaning liquid (sodium hydroxide) flow in the circuit, bag 31 is placed in communication with transfer section 22 by connecting the male coupling connector 34 to the female coupling connector 28. An intermediate female coupling connector (not shown in FIG. 1 for legibility) of section 22 situated between the transfer pump 25 and valve 26 is temporarily connected to an intermediate male coupling connector (not illustrated) of section 61 situated between the feed container 43 and the flow pump 64.

An intermediate male coupling connector of section 22, which is normally connected to the intermediate female coupling connector (not illustrated) is also temporarily connected to a second female coupling connector (not illustrated) of the waste container 74, connector 73 being connected to male coupling connector 86.

The transfer pump 25 is set to "open" position, such that all its rollers are away from portion 24a of pipe 24. Valves 44 and 69 are closed, the other valves being open.

The cleaning liquid is then driven by the flow pump 64 in the circuit and then is retrieved in waste container 74.

The cleaning liquid having being evacuated, the rinsing of the circuit is undertaken by connecting male coupling connector 35 of bag 32 to female coupling connector 28. The rinsing liquid is then driven by the flow pump within the circuit, then retrieved in waste container 74 in the same way as described previously for the cleaning operations.

As a variant, a first rinse is carried out of the circuit prior to the cleaning by passage of sodium hydroxide and/or the sodium hydroxide is flushed by the passage of air before the final rinsing.

The installation 1 that implements the circuit described above is described next with reference to FIGS. 2 to 8.

This installation 1 comprises two carts 2 and 3 each having a parallelepiped general shape and being of identical depth.

It is also to be noted that the first cart 2 extends over a much greater height above the ground than that of the second cart 3.

In order to facilitate its movement in the treatment area, the first cart 2 is mounted on wheels 200, and has two arcuate handles 200a which project from a first lateral face 202. It is hollow in order to receive certain elements of the circuit, and partly open at its front face 201 and at its lateral faces 202 and 203 in order to simplify the connection operations.

Cart 2 comprises (FIG. 2):
an inner metal chassis 204 partly covered by flat panels 205;
a feed tank 206 for receiving the feed container 43;
the electromagnetic drive 45;
the transfer pump 25 and flow pump 64;
an infrared temperature probe 211 (FIG. 3)
two horizontal trays 220 and 221 for respectively supporting the two pumps 25 and 64;
a vertical panel 223 bearing the valves 26, 44 and 54;
the flowmeter 85 (FIG. 7) disposed in a recess of the lateral face 203 located above pump 64; and
a control panel 230 to control in particular pumps 25 and 64 and to display the values measured in the circuit (pressure, temperature, volume, mass, flow rate, etc.), this panel 230 being disposed on the front face 201 above pump 64.

Tank 206 comprises a cylindrical lateral wall 206a of which one of the ends is extended by a frusto-conical bottom wall 206b provided with an oblong opening 206c (FIG. 3) for the passage of the apertures 43a and 43b of the flexible and disposable feed container 43, and two other circular openings 206d and 206e for the cooperation with the electromagnetic drive 45 and the temperature probe 211.

The tank 206 is pivotally mounted on the lateral uprights 207a of a U-shaped bracket 207 (FIG. 2) situated in a plane parallel to the lateral faces 202 and 203 of the cart 2 and of which the ends are fixed to a weighing balance frame 208 resting on supports 209 linked to the chassis 204.

Load cells 210 (FIG. 6) disposed between frame 208 and its supports 209 enable the mass of the tank 206 to be precisely determined.

Figure 4:
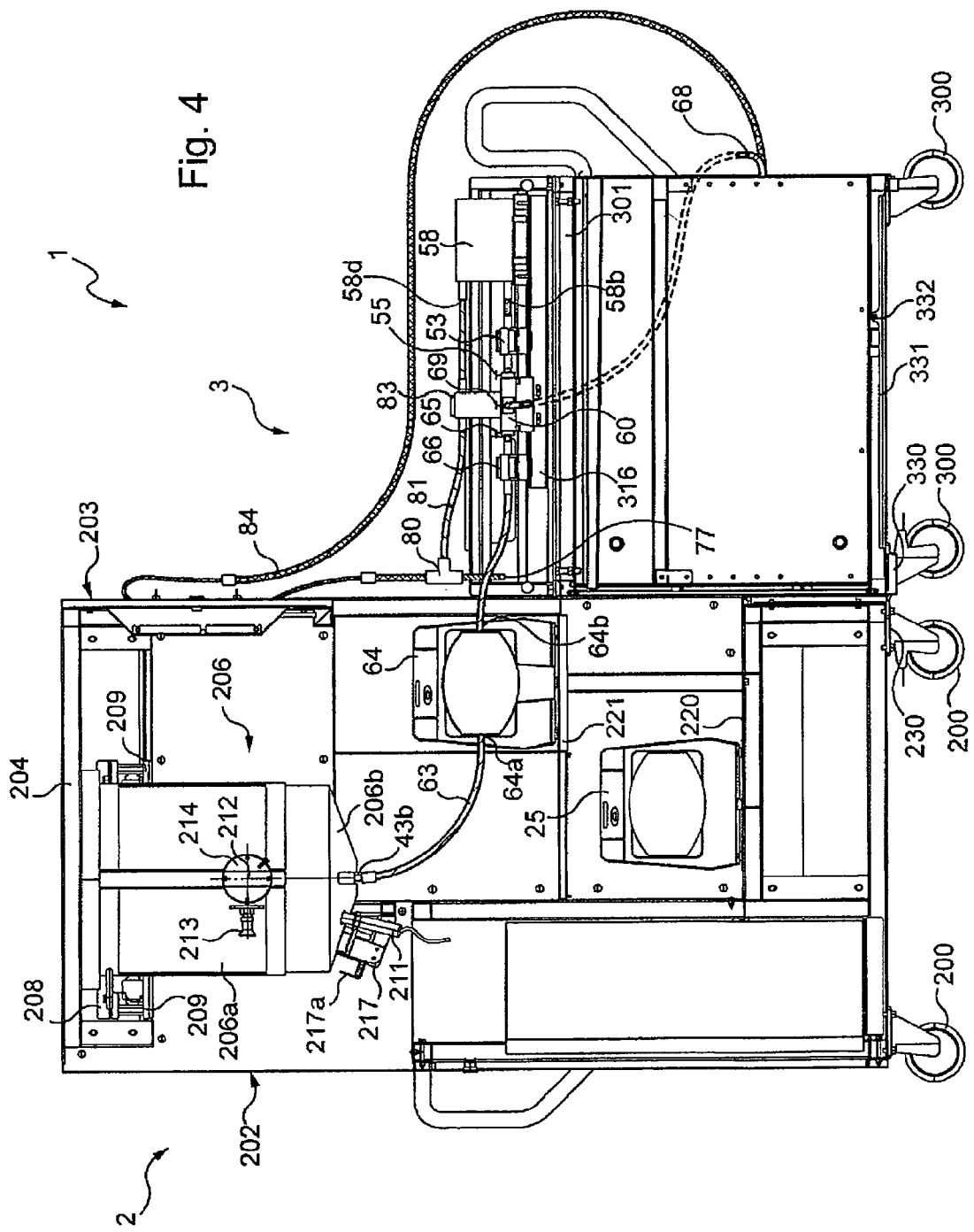
FIG. 4 is a cross-section view of that installation on plane IV-IV of FIG. 3.
Figure 5:
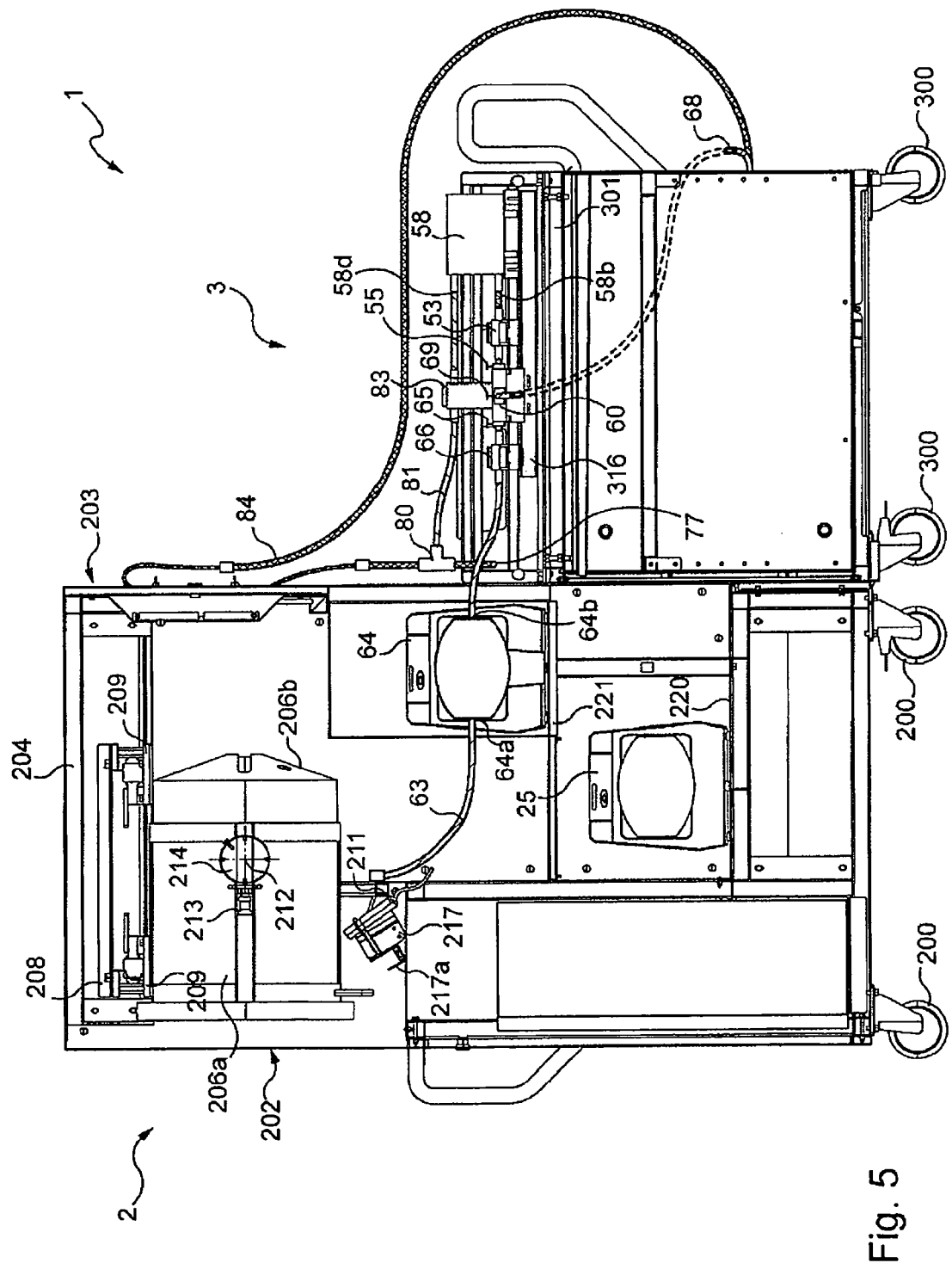
FIG. 5 is a cross-section view similar to that of FIG. 4, but in which the tank is in lying-down position, its bottom being directed towards the second cart.

A handle 206f (FIG. 3) fixed to the free end of the cylindrical lateral wall 206a of the tank 206 enables it to be easily pivoted about an axis 212 perpendicular to the front face 201, between an operating position (FIG. 4) and an installation position (FIG. 5). Two pins 213 (FIG. 3) disposed on each of the uprights of the bracket 207 in the vicinity of axis 212, are adapted to cooperate with two discs 214 fixed to the cylindrical lateral wall 206a of the tank 206 to lock it in the desired position, or, on the contrary, to free it to rotate.

The locking is achieved by the insertion of a metal rod situated at the end of each pin 213 into a bore 214a of the corresponding disc 214. Conversely, to free the tank 206 to rotate, it suffices to pull on each of the pins 213 in order to make the rods come out of the discs 214.

In its operating position, the tank 206 is upright, such that its frusto-conical bottom wall 206b is turned towards the ground; the feed container 43 being disposed within the tank 206, its apertures 43a and 43b projecting from that bottom wall 206b towards the ground.

In its installation position illustrated in FIG. 5, the tank 206 is lying down, the free end of its cylindrical lateral wall 206a then facing an opening 216 of the lateral face 202 of the cart 2. For the operator, this installation position facilitates the withdrawal of a spent feed container 43 and the installation of a new one.

The temperature probe 211 and the electromagnetic drive 45 serving for the actuation of the magnetically driven agitator 44, are fixed to a metal framework 217 (FIGS. 4 and 5) pivotally mounted on the cross-member 207b (FIG. 2) forming the base of bracket 207.

The infrared temperature probe 211 makes it possible to measure, through container 43, the temperature change of the biological liquid during its treatment.

The electromagnetic drive 45 (FIG. 2) comprises several spools making it possible to raise and turn the agitator 44 contained in the feed container 43.

Figure 2:
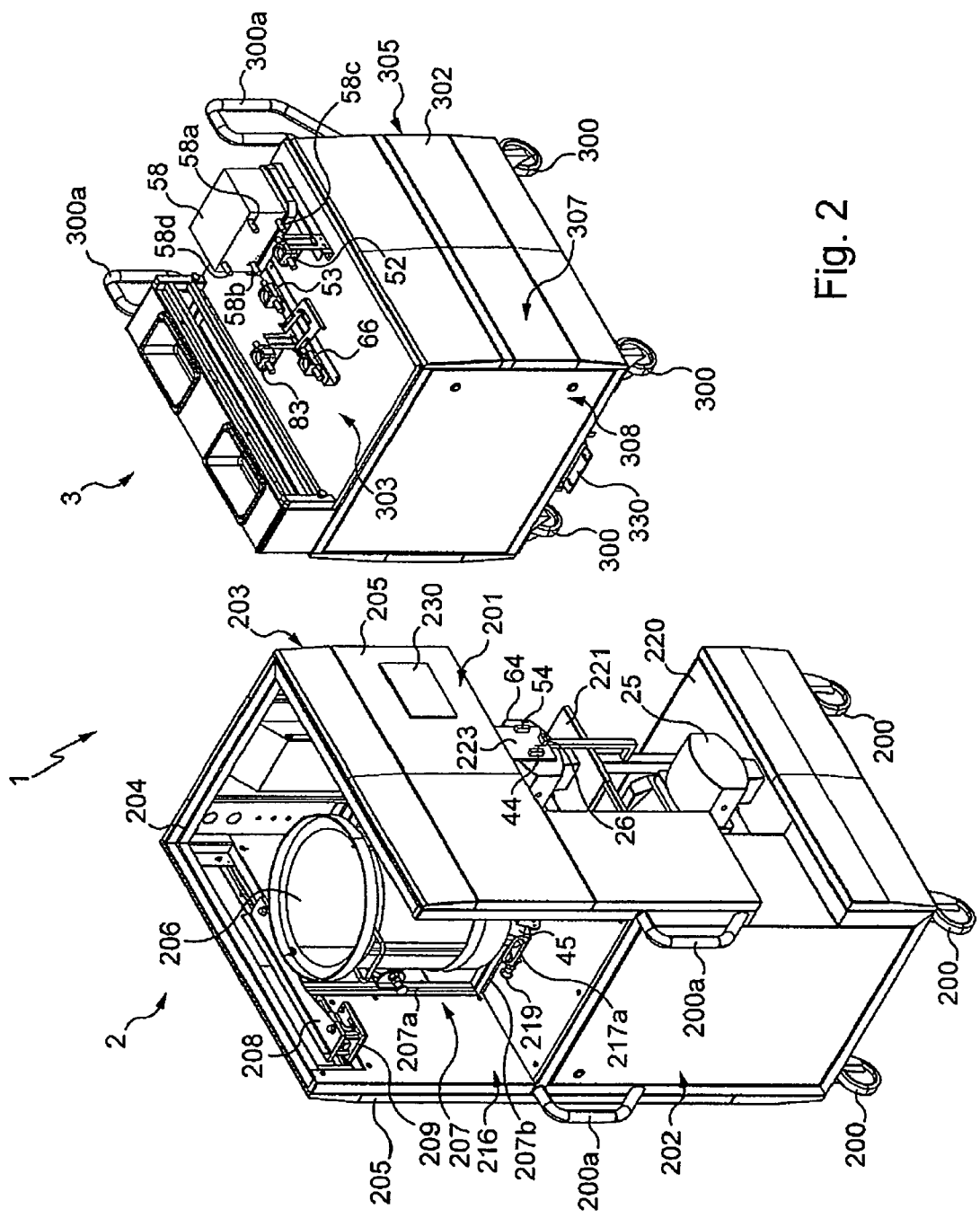
FIG. 2 is a perspective view of a first and of a second cart according to the invention in separated configuration.
Figure 3:
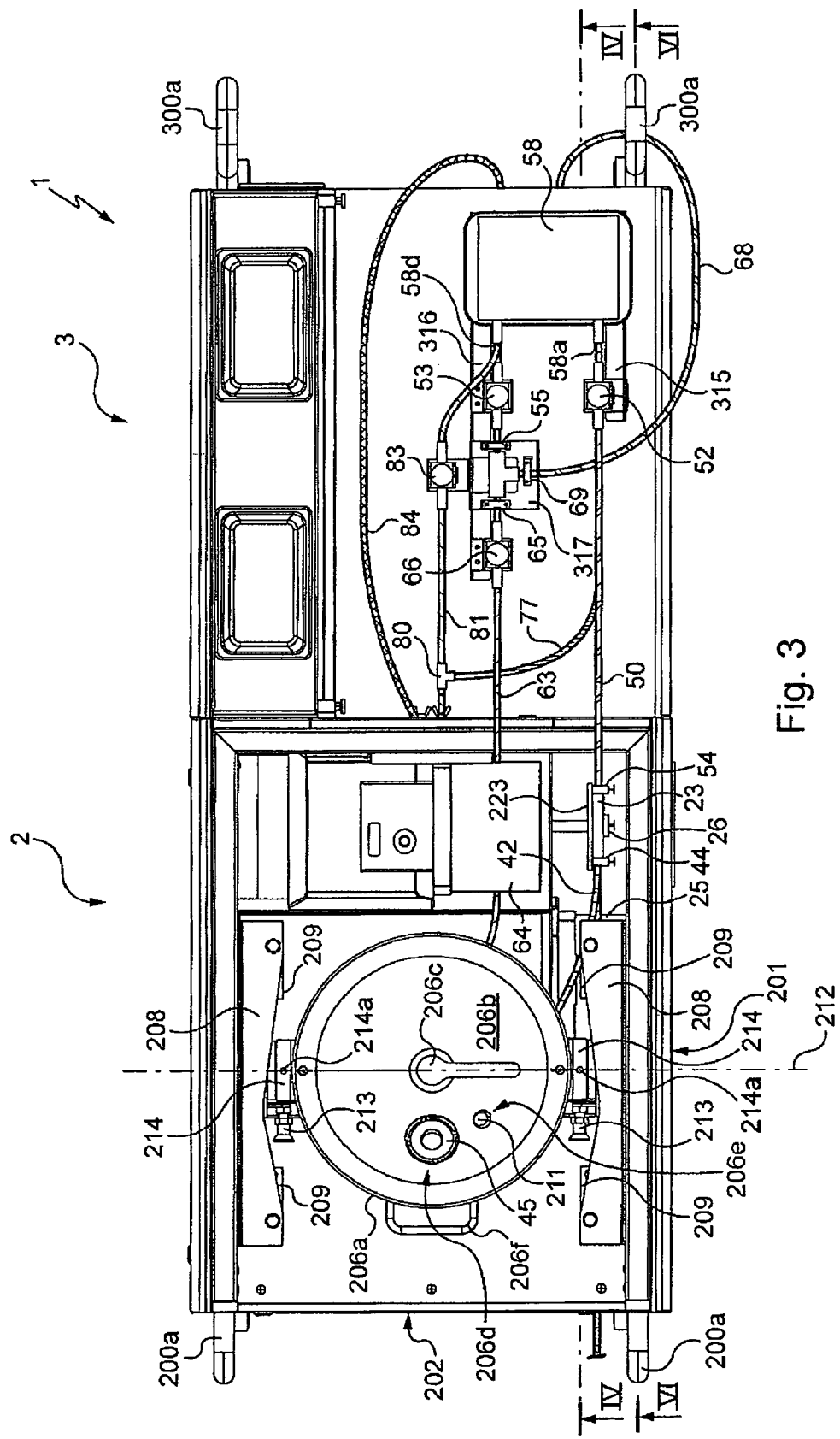
FIG. 3 is a view from above of the installation according to the invention comprising the two carts of FIG. 2 in juxtaposed configuration.

In putting the installation 1 into operation and after the tank 206 has been disposed in its operating position, the framework 217 is brought, using a handle 217a, to its position illustrated in FIGS. 2 to 4, in which the respective ends of the electromagnetic drive 45 and of the temperature probe 211 (FIG. 2) are positioned as closely as possible to container 43.

A pin 219 (FIG. 2) fixed to the cross member 207b is adapted to cooperate with the framework 217 in order to lock it in that position throughout the duration of the filtration process.

Once the process has been terminated, the framework 217 is unlocked to freely pivot and to find its equilibrium position in which it rests on the chassis 204 of the cart 2.

The cart 3 will now be described in more detail.

As for the cart 2, and in order to facilitate its movement in the treatment area, cart 3 is mounted on wheels 300, and has arcuate handles 300a which project from a first lateral face 305 (FIG. 2).

Figures 7, 8:
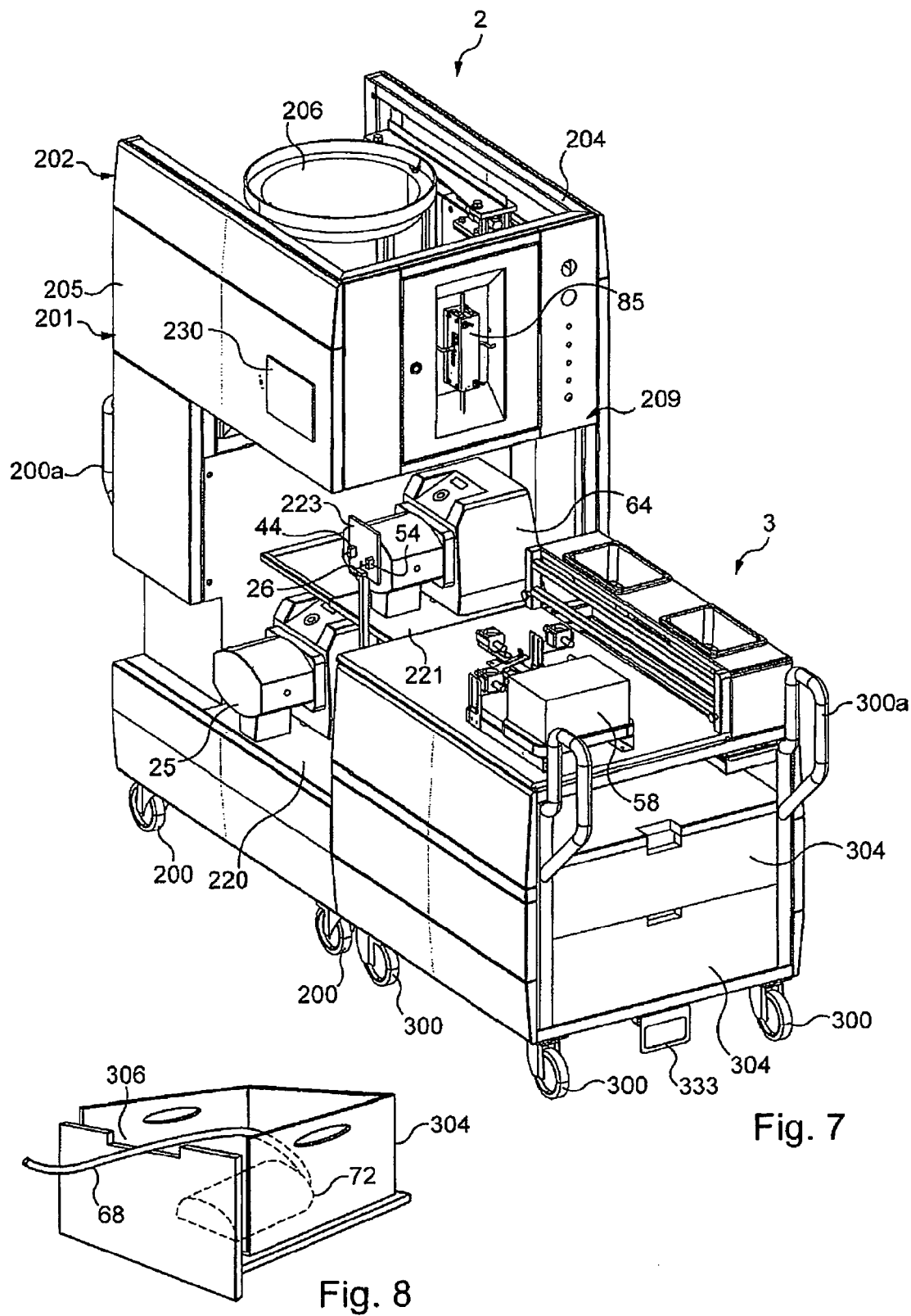
FIG. 7 is a perspective view from another viewing angle of the two carts of FIG. 2, in juxtaposed configuration.
FIG. 8 is a perspective view of a drawer of the second cart.

It comprises:
- an inner metal chassis 301 (FIG. 4) partly covered by flat panels 302;
- the supports for the connectors 52, 53, 66 and 83 for pressure sensors (although these connectors 52, 53, 66 and 83 are shown in FIGS. 3 and 7, they are disposable and are not permanently present on cart 3);
- the supports for valves 55, 65 and 69;
- two parallel arms 315, 316 fixed to the upper face 303 of that cart 3, and on which rest the disposable filter 58 and the supports for the connectors 52, 53, 66 and 83;
- a horizontal panel 317 extending from the arm 316 on which the supports for valves 55, 65 and 69 are fixed; and
- two storage drawers 304 (FIGS. 7 and 8) for storing the collecting 72 and waste 74 containers as well as any sampling or drainage containers, not illustrated for reasons of simplification.

The upper face 303 is entirely or partly formed by a plate of transparent material to enable the progress of the filling of the collecting container 72 to be followed.

The tangential filter 58 is disposed close to the first lateral face 305 and to the front face 307, its four apertures 58a, 58b, 58c and 58d being oriented towards the second lateral face 308 of cart 3.

The four supports for the connectors 52, 53, 66 and 83 are situated between the filter 58 and the second lateral face 308.

The storage drawers 304 are slidingly mounted in the internal part of the cart 3 and are accessible from its first lateral face 305 which is open. A cut-out 306 is provided in the facade of each drawer 304 in order to allow the passage of pipe 68 or 84 (FIG. 8).

On mounting the installation 1, the lateral face 203 of the first cart 2 is juxtaposed against the lateral face 308 of the second cart 3, as illustrated in FIGS. 3 to 7.

At the time of their juxtaposition, the carts 2 and 3 lock to each other, here by virtue of the engagement of an lug (not visible in the drawings) in an accommodation 330 (FIGS. 2 and 4) of cart 3.

The lug of cart 2 is situated at the end of a plate 230 (FIG. 4) fixed to the lower face of cart 2.

This lug projects from face 203 and at its center has an opening where one or more retaining teeth come to locate, which are situated at one of the ends of a lever 331 (FIG. 4) that is hinged on a pivot 332 carried by the lower face of cart 3. The other end of lever 331 is situated at lateral face 305 and comprises a pedal 333 (FIG. 7) enabling the lever 331 to be tipped to release the teeth from the opening of the lug projecting from cart 2, which enables the two carts to be freed.

Once the carts 2 and 3 have been juxtaposed, the disposable elements (pipes, containers, certain valves, connectors, filter, etc.) are installed on the re-usable elements disposed on the carts 2 and 3.

The mounting of the installation is then terminated and the installation is in accordance with FIGS. 3 to 6.

FIG. 4 which represents a cross-section of that complete installation with the pipes installed, enables it to be realized how the disposition of the two pumps 25 and 64 and of the tank 206 on cart 2 is optimized.

Thus the plate 221 which bears the flow pump 64 is disposed in the vicinity of lateral face 203 of cart 2 at a predetermined height and depth (relative to the front face 201) such that the outlet point 64b of the flow pump 64 is located substantially facing the inlet/outlet aperture 58b of the tangential filter 58 (FIG. 4). This positioning makes it possible to limit the length of the pipes 63 and 51 between the flow pump 64 and the filter 58, and thus the length of the sub-circuit in which the flow of the liquid occurs.

Similarly, the positioning of the tank 206 relative to the flow pump 64 makes it possible to limit the length of pipe 63 between the feed container 43 and pump 64, while taking into account the fact that this portion of pipe 63 has an elbow-shaped profile (since the outlet aperture 43b of container 43 is vertically oriented towards the ground, whereas the inlet point 64a of the flow pump 64 is horizontally oriented towards the tank 206).

More particularly, to avoid any risk of pinching of pipe 63, the radius of curvature of that elbow must be equal to or greater than a minimum value Rmin which depends on the characteristics specific to that pipe.

In other words, the outlet aperture 43b of container 43 must be offset in terms of height and in terms of width relative to the inlet point 64a of the flow pump 64, by at least that value Rmin.

Consequently, in order to meet this double offset constraint, the tank 206 (receiving container 43) is positioned above and laterally displaced (in the direction of the lateral face 202) relative to pump 64.

Figure 6:
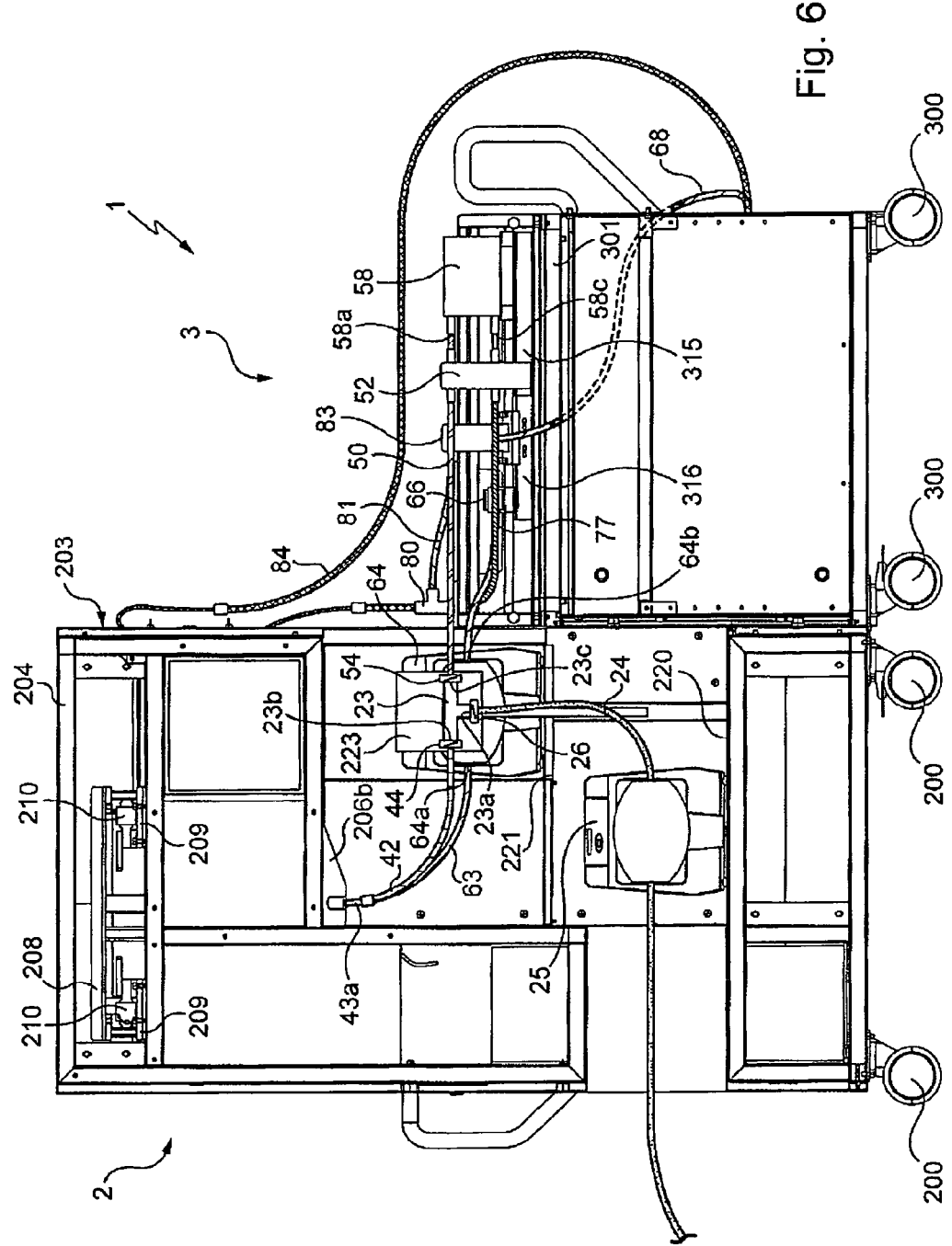
FIG. 6 is a cross-section view of that installation on plane VI-VI of FIG. 3.

Moreover, still with the object of limiting the length of pipe 50 between filter 58 and the branching connector 23, and thus the length of the sub-circuit in which the liquid is re-passed, this connector 23 must be disposed, on mounting the circuit, in the vicinity of lateral face 203 of cart 2, at a predetermined height and depth such that its aperture 23c is situated substantially facing the inlet/outlet aperture 58a of the tangential filter 58 (FIG. 6).

By looking at the filter 58 in FIG. 2, it can be noted that aperture 58a is situated slightly higher and further forward than aperture 58b. The aperture 23c of branching connector 23 (FIG. 6) must be positioned slightly higher and further forward than aperture 64b of pump 64.

Consequently, in order to meet this double offset constraint, the vertical panel 223 (on which is fixed branching connector 23) is positioned forward of pump 64 and at its upper portion (FIGS. 2, 6 and 7).

This constraint has an influence on the positioning of transfer pump 25 of which the inlet point 25b must be disposed in the same plane as the aperture 23a, 23c of branching connector 23 and the aperture 58a of the tangential filter 58 (FIGS. 3 and 6).

Pump 25 is thus offset towards the front relative to flow pump 64 such that it is disposed in the vicinity of the front face 201 of the cart (FIGS. 2 and 3).

The position of the transfer pump 25 must also take into account the fact that the portion of pipe 24 between the transfer pump 25 and branching connector 23 has an elbow-shaped profile since the aperture 23a of connector 23 is vertically oriented towards the ground whereas inlet/outlet point 25b of transfer pump 25 is horizontally oriented (FIG. 5).

In order to avoid any risk of pinching of pipe 24, the radius of curvature of that elbow must be equal to or greater than a minimum value R'min which depends on the characteristics specific to that pipe.

In other words, the inlet/outlet point 25b of transfer pump 25 must be offset vertically and in width relative to the aperture 23a of branching connector 23, by at least that value R'min.

Consequently, in order to meet this double offset constraint, transfer pump 25 is positioned below branching connector 23 (and thus below pump 64) and it is laterally displaced towards lateral face 202, which, furthermore, has the advantage of not increasing the width of the cart 2 which remains compact.

It will be noted that the advantage of minimizing the length of the filtration loop formed by sections 40, 41 and 61, is that at the end of treatment (feed container 43 empty or nearly so), the volume of biological liquid remaining in that loop is minimized too and the concentration attained is maximized. In variants that are not illustrated:

- rather than being horizontal, plate 221, is inclined such that it drops towards face 203, which is advantageous when section 63a of pipe 63 is curved within pump 64 such that its concavity is turned downwards (the rotor of pump 64 turning about a horizontal axis): this enables pump 64 to be inclined to avoid there being a low point in pipe 63 at inlet/outlet point 64a;
- section 22 is replaced by a similar section but comprising in addition a pressure sensor connector disposed between the second inlet/outlet point 25b of pump 25 and valve 26 in order to ensure proper operation of that pump 25;
- bags 30, 31 and 32 are permanently connected to transfer section 22, a set of valves positioned between those bags and section 22 making it possible to select the liquid that it is desired to pass in the circuit;
- valve 65 is eliminated, the blocking function simply being obtained by flow pump 64 when stopped;
- the peristaltic pumps 25 and 64 are replaced by pumps of another type, for example a pump adapted to receive a pumping head forming part of the disposable elements;
- when the volume of the source bag 20 is greater than that of the feed container 43, the operations for transfer of the liquid contained in that bag are carried out by the "fed batch" technique which consists of transferring only a part of the liquid from the source bag 20 into feed container 43, then of passing and concentrating that liquid in the sub-circuit formed by sections 40, 41 and 61 while progressively transferring (valve 26 remaining open) the rest of the liquid still contained in bag 20 which replaces the filtrate evacuated into waste container 74;
- connector 53 is eliminated, the pressure sensor connected onto connector 66 then being used to provide similar information;
- the connectors 21, 33, 34, 35, 70, 86, 28, 71 and 73 are replaced by fast connectors and/or non-male/female differentiated connectors;
- the flowmeter 85 is replaced by a weighing balance on which the collecting container 72 is placed in order to determine the mass and the rate of flow of the filtrate retrieved at the outlet of filter 58;
- other measuring and verification instruments are installed, for example an electrical conductivity or pH measuring cell, or even a cell for measuring the absorbency of the liquid by ultraviolet;
- drawers 304 are replaced by simple shelves which can be adjusted in height and on which roller mats and boxes are disposed in order to facilitate the positioning and withdrawal of containers 72 and 74;
- when the collecting 72 and waste 74 containers are too voluminous to be introduced inside cart 3, they are placed directly on the floor in the vicinity of that cart 3;
- the male coupling connectors 70 and 86 are linked to a drain;
- the metal framework 217 is replaced by a framework mounted so as to move vertically in translation relative to cross-member 207b;
- the filter 58, the connectors 52, 53, 66 and 83, and the valves 55, 65 and 69 are disposed on a simple table; and/or
- a final filter is disposed between valve 69 and the collecting container 72.

In other variants not illustrated, carts 2 and 3 may serve for carrying out different treatments than that of tangential filtration.

Numerous other variants are possible according to circumstances, and in this connection it is to be noted that that the invention is not limited to the example embodiments described and shown.

What is claimed is:

1. A cart for a biological liquid treatment installation comprising a first lateral face, a second lateral face by which it is adapted to be juxtaposed against another cart and a front face which meets the two said lateral faces;
said cart further comprising:
  a first pump;
  a second pump disposed below said first pump and laterally offset relative thereto towards said first lateral face; and
  a tank disposed above said first pump and offset laterally relative thereto towards said first lateral face, said tank being adapted to receive a feed container provided to contain said biological liquid and wherein said tank is movably mounted between an upright service position for operation and a lying-down installation position for the mounting or withdrawal of said feed container.

2. The cart of claim 1 wherein said tank is adapted to pivot about an axis perpendicular to said front face of said cart.

3. The cart of claim 1 wherein said tank has a device for locking said tank in either of the positions of service and installation.

4. The cart of claim 1 wherein said tank has a device for locking said tank in either of the positions of service and installation in the form of at least one pin.

5. The cart of claim 1 wherein said tank is mounted on a U-shaped bracket of which the ends are fixed to a balance frame adapted to cooperate with load cells to determine the mass of said tank.

6. The cart of claim 1 wherein said first and second pumps are peristaltic pumps.

7. An installation for treating a biological liquid, comprising:
  a cart for a biological liquid treatment installation having a first lateral face, a second lateral face by which it is adapted to be juxtaposed against another cart and a front face which meets the two said lateral faces;

said cart further comprising:
a first pump;
a second pump disposed below said first pump and laterally offset relative thereto towards said first lateral face; and
a tank disposed above said first pump and offset laterally relative thereto towards said first lateral face, said tank being adapted to receive a feed container provided to contain said biological liquid,
the cart designated first cart;
a filter; and
a second cart, juxtaposed against said first cart, and of which the upper supports said filter such that an outlet of said first pump is situated substantially facing an aperture of said filter.

8. The installation of claim 7 wherein said filter is a tangential filter.

9. The installation of claim 7 further comprising a container for collecting said filtered biological liquid after treatment, said collecting container being disposed in a housing of said second cart.

10. The installation of claim 7, further comprising a container for collecting said filtered biological liquid after treatment, said collecting container being disposed in a housing of said second cart and wherein said housing is formed by the interior of a drawer.

11. The installation of claim 7 further comprising a container for collecting said filtered biological liquid after treatment, said collecting container being disposed in a housing of said second cart, wherein said housing is formed by the interior of a drawer and a facade of said drawer comprises a cut-out through which a flexible disposable pipe from an outlet of the filter to the container passes.

12. The installation of claim 7 wherein the aperture of said filter is selected from the group consisting of an inlet and an outlet.

13. An installation for treating a biological liquid, comprising:
a cart for a biological liquid treatment installation having a first lateral face, a second lateral face by which it is adapted to be juxtaposed against another cart and a front face which meets the two said lateral faces;
said cart further comprising:
a first pump;
a second pump disposed below said first pump and laterally offset relative thereto towards said first lateral face; and
a tank disposed above said first pump and offset laterally relative thereto towards said first lateral face, said tank being adapted to receive a feed container provided to contain said biological liquid
the cart, designated first cart;
a filter; and
a second cart, juxtaposed against said first cart, and of which the upper face supports said filter such that an outlet of said first pump is situated substantially facing an aperture of said filter; the installation further comprising a source container for said biological liquid;
a feed container disposed in said tank of said first cart;
a container for collecting said filtered biological liquid;
a transfer section for connecting said source container to a first aperture of a branching connector comprising a member adapted to cooperate with said second pump of said first cart to make said biological liquid flow;
a filling section linking a second aperture of said branching connector to an aperture of said feed container; a filtration section comprising said filter and connecting a third aperture of said branching connector to a first aperture of a second branching connector; a feed section linking a second aperture of said second branching connector to an aperture of said feed container and comprising a member adapted to cooperate with said first pump of said first cart to make said biological liquid flow; and a section for collecting said filtered liquid to link a third aperture of said second branching connector to said collecting container; each of said transfer, filling, filtration, feed and collecting sections comprising at least one disposable pipe.

14. The installation of claim 13 further comprising at least one section for conveying the filtrate that serves to link an outlet of said filter to a waste container comprising at least one disposable pipe.

15. The installation of claim 13 further comprising at least one section for conveying the filtrate that serves to link an outlet of said filter to a waste container comprising at least one disposable pipe and wherein the at least one section comprises two said conveying sections extending from a respective said outlet of said filter and joining together via a branching connector so as to form a single section.

16. The installation of claim 13 wherein the aperture of said filter is selected from the group consisting of an inlet and an outlet and the aperture of said feed container is selected from the group consisting of an inlet and an outlet.

* * * * *

UNITED STATES PATENT AND TRADEMARK OFFICE
CERTIFICATE OF CORRECTION

PATENT NO. : 8,557,113 B2  
APPLICATION NO. : 12/592901  
DATED : October 15, 2013  
INVENTOR(S) : Jean Luc Beulay et al.

Page 1 of 1

It is certified that error appears in the above-identified patent and that said Letters Patent is hereby corrected as shown below:

Title page, in column 1, below item (65) insert item -- (30) Foreign Application Priority Data / Dec. 24, 2008 (FR) .......................................... 0859079 --, therefor.

In the Claims

In column 13, line 13, in claim 7 delete "upper supports" and insert -- upper face supports --, therefor.

Signed and Sealed this  
Fourth Day of March, 2014

Michelle K. Lee  
*Deputy Director of the United States Patent and Trademark Office*